(12) United States Patent
Laghi

(10) Patent No.: US 10,765,607 B2
(45) Date of Patent: Sep. 8, 2020

(54) THERMALLY ASSISTED THERAPEUTIC AIDS FOR COSMETICS AND WOUND TREATMENT

(71) Applicant: Alps South Europe S.R.O., Plzeň (CZ)

(72) Inventor: Aldo Laghi, Pinellas Park, FL (US)

(73) Assignee: ALPS SOUTH EUROPE S.R.O., Plzen (CZ)

( * ) Notice: Subject to any disclaimer, the term of this patent is extended or adjusted under 35 U.S.C. 154(b) by 0 days.

(21) Appl. No.: 16/007,643

(22) Filed: Jun. 13, 2018

(65) Prior Publication Data

US 2019/0336410 A1 Nov. 7, 2019

Related U.S. Application Data

(60) Provisional application No. 62/666,721, filed on May 4, 2018.

(51) Int. Cl.
*A61K 8/02* (2006.01)
*A61K 9/70* (2006.01)
*A61Q 19/00* (2006.01)

(52) U.S. Cl.
CPC .......... *A61K 8/0212* (2013.01); *A61K 8/0233* (2013.01); *A61K 9/7023* (2013.01); *A61Q 19/00* (2013.01)

(58) Field of Classification Search
CPC .............................. A61K 9/7023; A61Q 19/00
See application file for complete search history.

(56) References Cited

U.S. PATENT DOCUMENTS

| 5,424,519 | A | 6/1995 | Salee | |
|---|---|---|---|---|
| 6,319,599 | B1 | 11/2001 | Buckley | |
| 9,863,687 | B1 | 1/2018 | Sunol et al. | |
| 2003/0109910 | A1* | 6/2003 | Lachenbruch | A61F 5/0104 607/108 |
| 2004/0046147 | A1* | 3/2004 | Matsuda | C09K 5/063 252/70 |
| 2007/0277806 | A1* | 12/2007 | Dodo | A61F 7/034 126/263.02 |
| 2013/0085198 | A1 | 4/2013 | Ishigaki et al. | |
| 2016/0051402 | A1 | 2/2016 | Laghi et al. | |
| 2016/0374847 | A1* | 12/2016 | Lachenbruch | A61F 13/025 128/889 |
| 2018/0049914 | A1 | 2/2018 | Stewart | |

FOREIGN PATENT DOCUMENTS

DE 102010056029 A1 6/2012

\* cited by examiner

*Primary Examiner* — Jianfeng Song
(74) *Attorney, Agent, or Firm* — GrayRobinson, P.A.

(57) ABSTRACT

A permeable layer associated relative to a phase change material associated relative to a securing fabric layer. The permeable layer retains a therapeutic or cosmetic agent to be transferred, in whole or in part, to the user's skin. The phase change material may be dissolved within a thermoplastic matrix or situated within a suitable container. This invention provides the novelty of a phase change material, coupled with a permeable layer and a fabric layer, which work in conjunction with a therapeutic or cosmetic agent.

7 Claims, 3 Drawing Sheets

THERMALLY ASSISTED THERAPEUTIC AIDS FOR COSMETICS AND WOUND TREATMENT

CROSS-REFERENCE TO RELATED APPLICATIONS

This application claims priority to provisional application No. 62/666,721, filed May 4, 2018, the disclosure of which is incorporated by reference herein.

BACKGROUND OF THE INVENTION

Field of the Invention

This invention relates to therapeutic aids for cosmetic and wound treatment. More specifically, this invention relates to a layered therapeutic aid comprising a phase change material ("PCM"), a permeable material in association with a therapeutic or cosmetic agent, and an optional securing fabric.

Description of the Background Art

It is well known that localized high temperatures increase blood flow and adsorption rates of therapeutic agents. Further, localized low temperatures reduce inflammation and bacterial growth. Thus, it is important to be able to use hot or cold temperatures during treatments of varying complexities.

Typically, injuries require a substantial amount of hot/cold treatments and accompanying therapeutic moisturizers, creams, etc. Currently, treatment products are unable to retain the moisturizer, cream, therapeutic or cosmetic agents, on the hot/cold surface of the object during the lengthy application to the user.

Phase change materials are commonly used to in these applications because of their ability to change from liquid to solid at a certain temperature. However, these phase change materials have three noteworthy shortcomings. First, they become liquid at low temperatures, at or around the melting temperature water, 0° C. As a result, the materials are not self-containing. To overcome this, the materials are often contained in a container, bag or similar impermeable structure. As a result of the impermeable structure, the thermal exchange properties are altered due to the barrier between the bodies exchanging heat. Additionally, the impermeable structure limits the ability of the phase change material to conform to uneven surfaces. Secondly, the described water-based phase change materials exhibit high thermal conductivity, which results in accelerated transfer of heat. In instances related to living organisms, tissue, and the like, this can result in damage or premature expiration. Lastly, many of the water-soluble salt phase change materials are not safe for contact with living organisms, tissue, or the like. Thus, the impermeable structure must be designed to minimize the possibility of puncture or exposure to the intended body for which the heat exchange is to occur. Also these water based material when frozen are hard solids and cannot be made to conform to the body topography.

In a prior invention, a thermoplastic elastomer comprising a triblock copolymer, was disclosed, and is reflected in U.S. application Ser. No. 14/602,894 ("'894 application") entitled "Post-Surgical Articles for Reduction of Swelling, Edema, and Bruising", filed on Jan. 22, 2015, and is hereby incorporated by reference herein. The disclosed invention in the '894 application provided a means of warm thermal therapy for various types of post-surgical procedures for reducing the negative after-effects of an operation, such as edema and swelling. The invention was able to achieve this by utilizing the conformability, durability, and low thermal conductivity of a phase change material situated within an elastomeric matrix, as compared to other hydro gel and water-based substances.

Therefore, it is an object of this invention to provide an improvement which overcomes the aforementioned inadequacies of the prior art devices and provides an improvement which is a significant contribution to the advancement of therapeutic aids for cosmetic and wound care.

It is a further object of this invention to provide a PCM associated relative to a permeable layer, which incorporates a therapeutic or cosmetic agent.

It is a further object of this invention to provide a permeable layer that allows a therapeutic or cosmetic agent to be transferred, in whole or in part, to the user over a specified time interval.

It is a further object of this invention to provide a garment or fabric layer incorporating the PCM and permeable layer.

It is a further object of this invention to provide a therapeutically effective garment or fabric layer using a PCM and permeable layer that is comfortable for a user to put on their skin.

It is a further object of this invention to provide a garment that can be used to treat facial injuries as well as dermatological procedures such as chemical peels and dermabrasion and therapeutic treatments at establishments such as salons and spas.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention discloses a layered therapeutic aid comprising a phase change material dissolved in a low modulus elastomer, a permeable material in association with a therapeutic or cosmetic agent and optionally a strapped fabric.

This invention combines a source of heat or cooling, supplied at a constant temperature, with therapeutic or cosmetic agents able to transfer from the invention to the user.

The present invention overcomes the aforementioned inadequacies and provides a novel solution to the described deficiencies. The present invention utilizes a phase change material, a permeable layer and a fabric. The PCM may be dissolved in a thermoplastic matrix as described in the '894 application or may be contained within a suitable container. Specifically, the triblock copolymer is a styrene-based polymer. Within the thermoplastic elastomer is a lipid or a combination or association of one or more ligands that change phase from solid to liquid at certain temperatures. For cold applications, the lipid changes phase at a temperature range of −10° C. to 25° C. and preferably between 0° C. to 20° C. For heat applications, the lipid changes phase at 45° C. to 65° C.

Embodiments of the present invention are herein described by way of example and directed to a phase change material utilizing an elastomeric matrix having lipids that change phase from solid to liquid at a low and high temperatures, which is then associated relative to a permeable layer, The aforementioned state of the art of phase change materials shows the need for improvements in phase change materials that can allow a therapeutic or cosmetic agent to be uniformly transferred, in part or in whole, from the permeable layer to the user, with varying heat and/or cold applications.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which.

DETAILED DESCRIPTION OF THE PREFERRED EMBODIMENT

Figure 1:
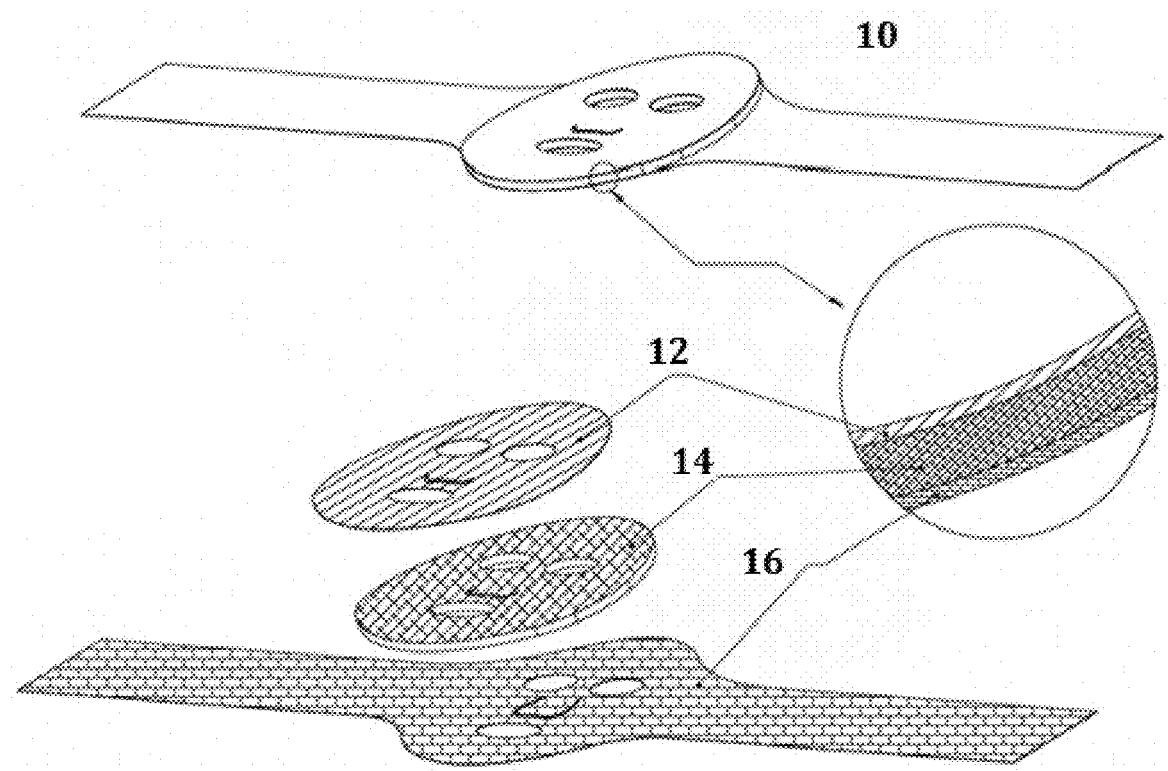
FIG. 1 depicts a thermally assisted therapeutic aid, in the shape of a facial mask, for cosmetic and wound treatments in an exploded view and in composite form.

The following description is of the best mode presently contemplated for carrying out the invention. This description is not to be taken in a limiting sense, but is made merely for the purpose of describing one or more preferred embodiments of the invention. The scope of the invention should be determined with reference to the claims.

In certain aspects, the preferred elastomer is a triblock copolymer of styrene end blocks and mid blocks chosen from any of the following: polyethylene, polypropylene, polybutadiene, polybutylene, or combinations or equivalents thereof.

In certain aspects, the layer of permeable material may be composed of an open cell foam, felt and/or knit and/or weave of hydrophobic or amphiphilic or hydrophilic fibers, and/or non-woven fabric.

In certain aspects, the preferred PCMs are as follows: for heat application, hydrocarbon waxes which melt in the range of 45° C. to 65° C., and for cold application, linear alpha olefins which melt in the range of 0° C. to 20° C.

Notably, these waxes and linear alpha olefins are miscible completely in the polymer matrix, thus not requiring a containing bag. Furthermore, they are non-toxic and safe to human tissue, thus no barrier is required between the elastomer and human tissue. The thermal conductivity of these elastomers is much lower than the conductivity of water or ice, therefore they provide a comfortable source of heat or cold at a constant temperature, without the need for a thermal barrier such as cloth or plastics.

The therapeutic or cosmetic agent is dissolved into a liquid solution, which is then placed relatively within the permeable material. The solvent used in the liquid solution may be a lipid or electrolytic type. The liquid solution is then incorporated relative to the layer of permeable material, such that the permeable material retains the liquid solution.

For example, benzoyl peroxide, salicylic acid and/or azelaic acid may be used as a therapeutic agent, coupled with heat, for the treatment of acne. Any and all equivalents of the mentioned therapeutic agents may also be used.

For example, tocopherol, antiseptics, antibiotics and/or any equivalents may be used as a therapeutic agents, coupled with cold, for the treatment of the body after surgery, dermabrasion, skin peel, and/or any and all equivalents.

The PCM, with the thermoplastic matrix described in the '894 application, is bonded to the layer of permeable material by means of adhesives or by casting or molding the elastomer onto the permeable layer or by heat bonding the elastomer to the permeable layer.

If no shaping is required then the PCM of already used industry materials, such as pads for heating or cooling parts of the body such as the upper and lower torso, can be used when enclosed in a suitable container. Once the PCM is bonded or associated relative to the permeable layer, then the therapeutic or cosmetic agent is incorporated relatively within the permeable layer. If the PCM does not require a thermoplastic matrix as described in the '894 application, then the layer of permeable material is bonded to the container that holds the PCM.

FIG. 1 shows a three layer embodiment of a thermally assisted therapeutic aid 10. The aid 10 is composed of up to three layers, one being a permeable layer 12, which is located relative to a PCM layer 14, which can be located relative to an optional securing fabric layer 16. These three layers may be situated interchangeably depending on the user's needs. Furthermore, multiples of each layer may be used depending on the user's needs. For example, more than one permeable layer 12 may be needed if the user requires more therapeutic agent to be transferred to their injured area.

The permeable layer denoted as "G" of the invention can be physically interlocked with the PCM layer denoted as "M" and physically interlocked with the fabric layer "F" to form composites as denoted for simplicity by their combinations GM, GMG, MGM, MGG, GGM, MMMG, MMMGM, MGGM, GMGG, GMMG, GGMM, GGMGM, GMGMM, MGMGMG, GGMMG, GGMGMG, GMF, GMGF, MGMF, MGGF, GGMF, MMMGF, MMMGMF, MGGMF, GMGGF, GMMGF, GGMMF, GGMGMF, GMGMMF, MGMGMGF, GGMMGF, GGMGMGF, and the like or any of their permutations of one or more G with M.

Figure 2:
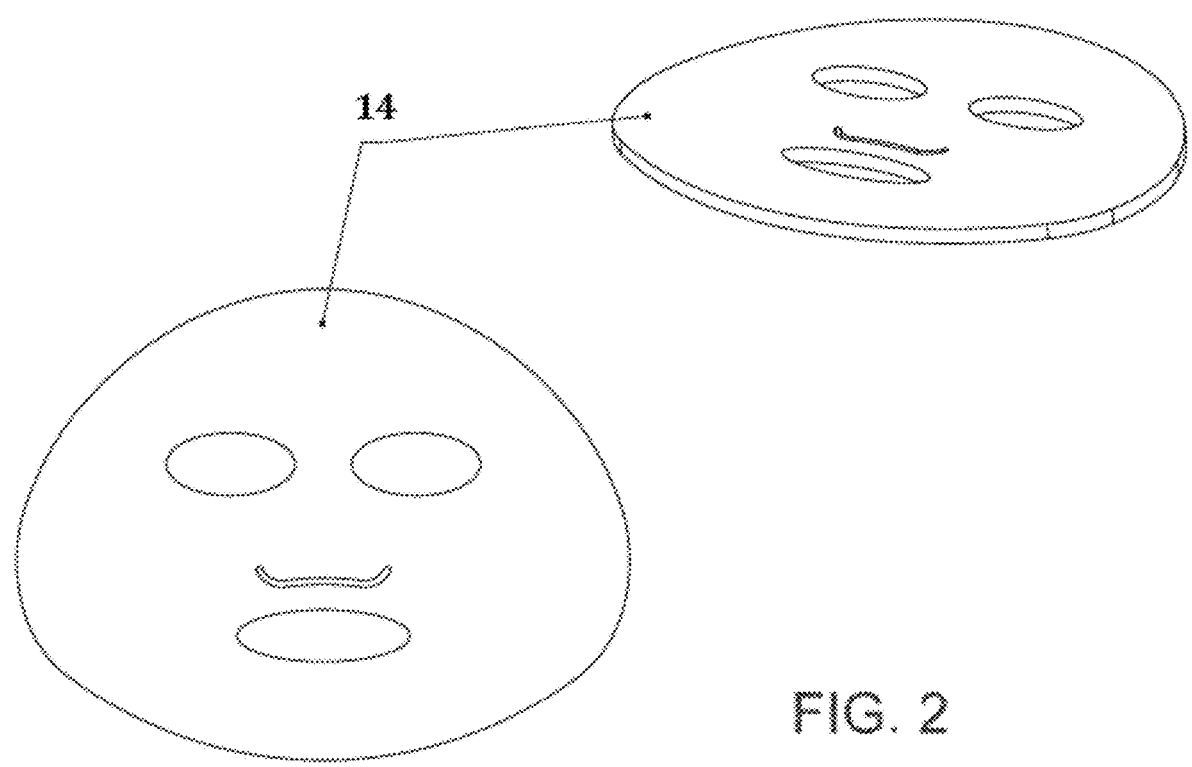
FIG. 2 depicts the phase change material.

FIG. 2 shows the PCM layer 14, which may or may not be located or attached to a thermoplastic matrix.

Figure 3:
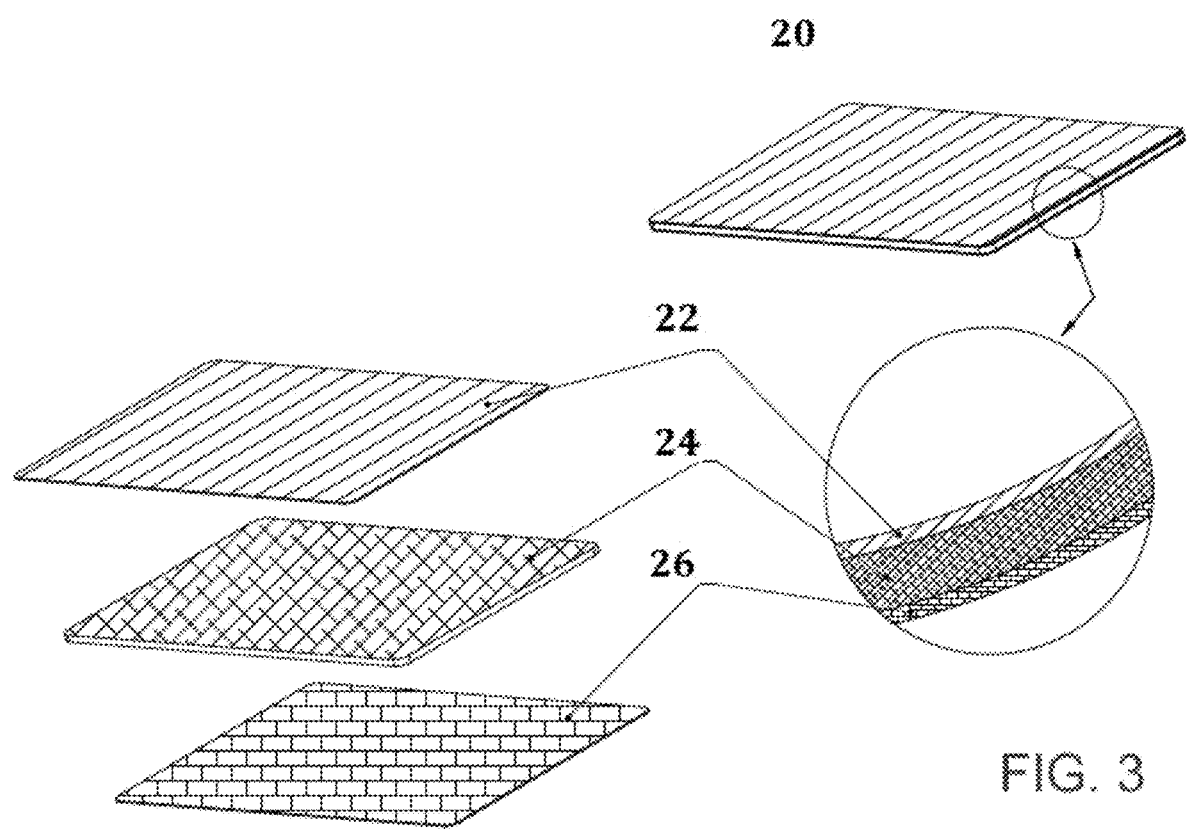
FIG. 3 depicts a thermally assisted therapeutic aid, without regard to a specific shape, for cosmetic and wound treatments in an exploded view and in composite form.

FIG. 3 shows an up to three layer embodiment of a thermally assisted therapeutic aid without regard to shape 20. The aid without regard to shape 20 is composed of up to three layers, one being a permeable layer 22, which is located relative to a PCM layer 24, which is then located relative to a securing fabric layer 26. These three layers may be situated interchangeably depending on the user's needs. Furthermore, multiples of each layer may be used depending on the user's needs. For example, more than one permeable layer 22 may be needed if the user requires more therapeutic agent to be transferred to their injured area.

In certain embodiments, the present invention may be configured to be placed within or onto a fabric, structure, garment, or any equivalent that is used for the purposes of contacting a user. The fabric, structure, garment, or any equivalent may be secured to the user by way of straps, strings, hook and loop fasteners, such as Velcro, magnets, rivets or any equivalent fastening means. Also, the fastening means may include techniques that allow the material to be situated within another material, such as a bag, towel, paper cloth, or any equivalent, which is then collectively secured or introduced to the user. For example, a user may place the present material into a damp towel, which is then situated to rest on her foot. Further, the securing of the disclosed invention may be accomplished without such fastening means, especially if the materials are configured to conform to the user's geometry or dimensions.

In certain embodiments, the present invention may be configured to form to a user's face, head, neck, upper or lower torso, feet, legs, or arms, or any combinations thereof. The user's specific needs for using the present invention will dictate its geometric form.

What is claimed is:

1. A thermally assisted therapeutic aid comprising:
    a single, contiguous, material layer, wherein the material layer is composed of an open cell foam, felt, knit, weave of hydrophobic or amphiphilic or hydrophilic fibers, non-woven fabric or their combinations thereof comprising a therapeutic agent homogeneously dissolved in the material layer;
    a phase change material layer comprising a phase change material; and
    a fabric layer configured to secure the aid relative to an appendage.

2. The thermally assisted therapeutic aid of claim 1 wherein the phase change material is situated within a container.

3. The thermally assisted therapeutic aid of claim 1 wherein the phase change material is bonded to a container that contains the phase change material.

4. The thermally assisted therapeutic aid of claim 1 wherein the phase change material is situated within an elastomeric matrix.

5. The thermally assisted therapeutic aid of claim 1 wherein the phase change material is a linear alpha olefin having a melting point in the range of 0° C. to 20° C.

6. The thermally assisted therapeutic aid of claim 1 wherein the phase change material includes a hydrocarbon wax having a melting point in the range of 45° C. to 65° C.

7. The thermally assisted therapeutic aid of claim 1 wherein the phase change material layer is bonded relative to the material layer by means of adhesives, casting, molding, or heat treatments.

* * * * *